(12) United States Patent
Hjertman et al.

(10) Patent No.: US 8,535,274 B2
(45) Date of Patent: Sep. 17, 2013

(54) SYSTEM AND METHOD FOR MODIFICATION OF A DEVICE AND A DEVICE SUITABLE FOR MODIFICATION

(75) Inventors: Birger Hjertman, Vallingby (SE); Hans Himbert, Bromma (SE); Bohdan Pavlu, Nacka (SE); Kerstin Genetay, Drottningholm (SE)

(73) Assignee: Pfizer Health AB, Stockholm (SE)

( * ) Notice: Subject to any disclaimer, the term of this patent is extended or adjusted under 35 U.S.C. 154(b) by 956 days.

(21) Appl. No.: 12/107,488

(22) Filed: Apr. 22, 2008

(65) Prior Publication Data

US 2008/0195052 A1 Aug. 14, 2008

Related U.S. Application Data

(63) Continuation of application No. 10/414,673, filed on Apr. 16, 2003, now abandoned.

(60) Provisional application No. 60/374,348, filed on Apr. 22, 2002.

(30) Foreign Application Priority Data

Apr. 16, 2002 (SE) ........................ 0201142

(51) Int. Cl.
*A61M 5/00* (2006.01)

(52) U.S. Cl.
USPC .......................... 604/187; 604/189

(58) Field of Classification Search
USPC ............... 604/187, 189, 227; 16/430
See application file for complete search history.

(56) References Cited

U.S. PATENT DOCUMENTS

| 2,586,581 A | 2/1952 | Tschischeck |
| 2,730,099 A | 1/1956 | Sullivan |
| 4,148,316 A | 4/1979 | Zanthopoulos |
| 4,582,488 A | 4/1986 | Newman |
| 4,743,234 A | 5/1988 | Leopoldi et al. |
| 5,297,980 A | 3/1994 | Barthold |
| 5,364,267 A | 11/1994 | Fischer |
| 5,520,658 A | 5/1996 | Holm |
| 5,595,566 A | 1/1997 | Vallelunga et al. |
| 5,651,775 A | 7/1997 | Walker et al. |

(Continued)

FOREIGN PATENT DOCUMENTS

| GB | 2292524 A | 2/1996 |
| WO | WO98/43690 | 10/1998 |

(Continued)

*Primary Examiner* — Kevin C Sirmons
*Assistant Examiner* — Deanna K Hall
(74) *Attorney, Agent, or Firm* — Dinsmore & Shohl LLP

(57) ABSTRACT

The injection device comprises a housing designed or suitable for manual gripping, a container for a preparation attached/enclosed in the housing, an outlet for the preparation exposed with respect to the housing and a mechanism arranged for moving the preparation at least from the container through the outlet. The system comprises a set of at least two elements having different properties in at least one respect. The elements are designed for mechanical attachment to one and the same area part of the housing, one at the time. The method includes the steps of providing at least two elements having different properties in at least one respect, the elements being designed for mechanical attachment to one and the same area part of the housing, one at the time, selecting one element from the set, and attaching mechanically the selected element to said area part of the housing.

22 Claims, 2 Drawing Sheets

(56) References Cited

U.S. PATENT DOCUMENTS

| | | | |
|---|---|---|---|
| 5,728,074 A * | 3/1998 | Castellano et al. | 604/207 |
| 6,454,746 B1 * | 9/2002 | Bydlon et al. | 604/227 |
| 6,685,678 B2 | 2/2004 | Evans et al. | |
| 2002/0188259 A1 | 12/2002 | Hickle et al. | |
| 2004/0107543 A1 * | 6/2004 | Ruana | 16/431 |
| 2005/0119622 A1 | 6/2005 | Temple | |

FOREIGN PATENT DOCUMENTS

| | | |
|---|---|---|
| WO | WO98/55168 | 12/1998 |
| WO | WO99/59657 | 11/1999 |
| WO | WO00/77085 | 12/2000 |
| WO | WO01/91833 | 12/2001 |

* cited by examiner

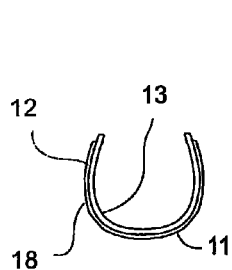
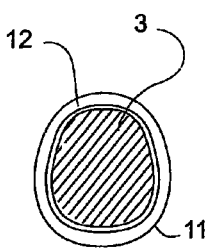
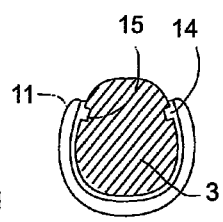
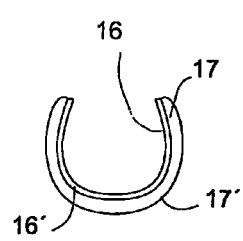
Fig. 5  Fig. 6  Fig. 7  Fig. 8
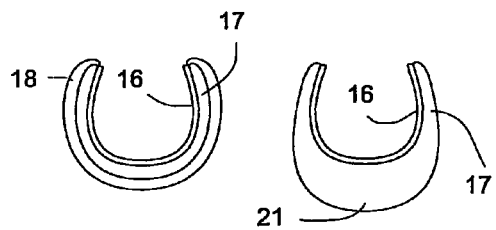
Fig. 9  Fig. 10  Fig. 11  Fig. 12
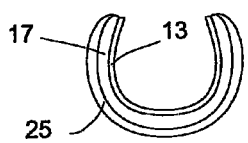
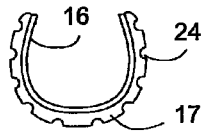
Fig. 13  Fig. 14
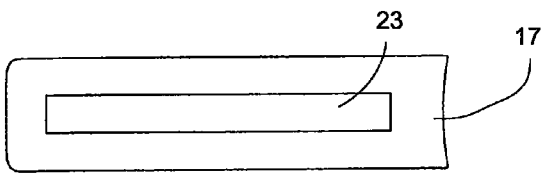
Fig. 15
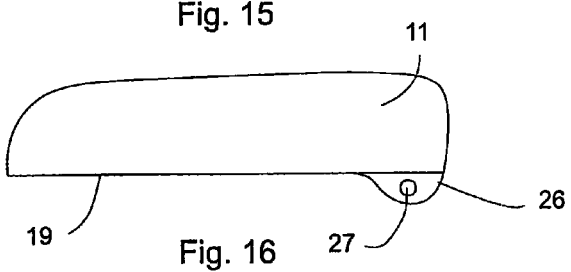
Fig. 16

SYSTEM AND METHOD FOR MODIFICATION OF A DEVICE AND A DEVICE SUITABLE FOR MODIFICATION

RELATED APPLICATIONS

The present application is a Continuation of U.S. application Ser. No. 10/414,673 filed Apr. 16, 2003 which claims priority under 35 U.S.C. §119 of Swedish Patent Application No. 0201142-7 filed Apr. 16, 2002 and U.S. Provisional Patent Application Ser. No. 60/374,348 filed Apr. 22, 2002. The entire disclosures of which are hereby incorporated by reference.

TECHNICAL FIELD

Present invention is directed to a system and a method for modification of an injection device, and an injection device suitable for modification the injection device comprising a) a housing designed or suitable for manual gripping, b) a container for a preparation attached to or enclosed in the housing, c) an outlet for the preparation exposed with respect to the housing, d) optionally a cap or guard arranged for removable attachment over the outlet and e) a mechanism arranged for moving the preparation at least from the container through the outlet.

BACKGROUND OF THE INVENTION

Existing portable multidose apparatuses or injection devices, eg. pen-type injectors, generally consists of a first end portion with an ejection outlet, e.g. a mounting for a needle assembly, a second, opposite end portion possibly having a dosing button, and an intermediate portion serving as a handle. Said portions are integrated in a common shell-type housing of non-flexible resin, preferably an injection moulded casing. The design of the casing is adapted to protect the injector from damages when being dropped on a floor or when being subjected to bending or twisting forces, as the hard casing resists the contemplated applied forces and shelters the mechanism of the injector. However, all pen-type injectors of the same brand are identical resulting in confusion which injector belongs to who when two or more injectors at the same time and for some reason are present in the same location. Further, different individuals may need functional adaptations to there specific requirements, e.g. in respect of added feature or adapted size and shape for gripping parts. PCT application WO 98/55168 is directed to a manually operated injection apparatus having an injection moulded housing with an intermediate handle portion. A soft-touch semi circular layer is firmly attached to a part of the handle portion by for example a two-shot moulding or co-injection moulding process. This means that the injection apparatus is obtainable with a permanently fixed grip of a soft-touch semi circular, in cross section, layer. However, this grip is of a standardized design and can not be adapted to a users personal requirements or needs. Further, every injection apparatus of the same brand looks alike and are hard to distinguish from each other.

It is an object of present invention to provide an element for a manually operated injection device, which is customized to the user's personal requirements and wishes.

It is an other object of present invention to provide an element for an injection device holding information concerning the owner of the device, dose and kind of medical drug to be delivered to the owner in case of emergency and other vital information.

A further object of present invention is to provide an element for an injection device in which a metering device is integrated.

These and other objects to be evident form the description below are met by the characteristics set forth in the appended claims.

Known in the art are various consumer articles, e.g. cell phones etc., marketed with a plurality of add-on parts allowing the article to be personalized or customized. Typically such add-ons only serve an aesthetical but not a functional purpose. Furthermore, faulty handling, misuse, unauthorized access or inadvertent mix-up of different individuals articles does not cause harm. In contrast, manually operated injectors may bring severe harm if not properly handled before, during and after injection. A patient identifying the wrong device is an obvious risk factor. Preparatory steps may include for example needle attachment, mixing, dose setting and deaeration of the preparation, arming of the device etc. Critical steps in the mere injection phase can be steady abutment to or penetration of the proper target site, penetration to proper depth, possibly aspiration of body fluid, delivery of full dose and withdrawal without residue. After the treatment it may be necessary to remove a contaminated needle, clean and reset the device, replace a preparation ampoule or store the device with ampoule in a refrigerator. All such steps may cause harm, e.g. by over or under dosing, destruction of tissue, injection of air, transmittal of blood borne infections or deactivation of drug. Manually operated injectors must be designed for worst-case situations including self-administration also by children, elderly and disabled persons, even when traumatized by the injection procedure itself. Optimization of a design for all possible patient and assistant groups is difficult, however. There are individual variations in hand sizes, gripping patterns, body postures and administration regimens. Patients dependent on daily administrations also have a legitimate right for consideration to individual variations in taste and preferences, e.g. for devices that need to be brought around in daily life.

SUMMARY OF THE INVENTION

The present invention serves to solve the above-indicated problems in connection with injection devices. The invention provides a system and a method for modification of injector devices allowing variation of device properties within broad ranges. The invention offers a plurality of elements that can be attached to an injector housing. With elements having different properties a multitude of variations becomes possible for the housing part of the device, which shall be illustrated and exemplified in the detailed description below. Device size and/or shape can be affected. For example, the size of the device can be adapted to the size of individual hands, even continuously as for a growing child, or to gripping habit variations such as when using precision grip, as when using a pen, or force grip, as when using the hole first. Even adaptations to individual normal, disabled or injured hand shapes become possible. Soft or sensitive materials can be used as a worn or destroyed element can be replaced. Elements used e.g. at gripping areas with textured surfaces can be removed and cleaned or sterilized separately even when the injector as such does not stand such treatment. Individual shapes can be used e.g. to allow identification also by a blind patient. Size and shape variations are possible also when the housing has a specific site for the element, e.g. with locking or guiding structures, as the element can extend beyond the site to varying degrees. The element can also be used to carry information of general or individual character and in human or machine readable form, the latter e.g. for security or physician verification. Aesthetic variations of individual taste can also be said to carry information. The element can also be used to add a functional property as in case of metering devices. For example, an element including a thermometer function, e.g. including liquid crystals, may help a patient verifying that the device is stored under suitable cold conditions, that it is not or has not been exposed to drug destroying temperatures or that the device has regained suitable temperature for injection. Further examples will be given below.

As indicated, a manually operated injection device can be said to comprise a) a housing designed or suitable for manual gripping, b) a container for a preparation attached to or enclosed in the housing, c) an outlet for the preparation exposed with respect to the housing, d) optionally a cap or guard arranged for removable attachment over the outlet and e) a mechanism arranged for moving the preparation at least from the container through the outlet. For description purposes the housing a) shall be regarded as providing an "encasing" function whereas the other elements b), c), d) and e) provides "operative" functions, not forming part of the housing.

The principles of the present invention may be used for injection devices or systems in broad terms utilizing various delivery principles. The device may be of disposable design but is preferably designed reusable. The device is manually operated in the sense that it shall at least be gripped, typically in connection with an injection step, but may also require additional handling steps. The injector can be entirely manually operated, e.g. wherein a control button is pushed to perform injection and possibly also manipulated to set a dose etc. The device can be more or less automatic with mechanical means, such as in autoinjectors, or with electronic and motorized means. The housing shape can vary depending on internal layout but shall have a basic form suitable for gripping. It may have the elongated and even generally cylindrical form known from injection pens. Although the elements of the present system may add to housing ergonomics and convenience properties it is preferred that can be manually operated also without such elements, e.g. for minimum size in the hands of a child. The container can be any type of single use, refillable or replaceable. Syringe type containers can be used, such as ampoules, cartridges, carpoules and syringes. The outlet from the device may be an infusion channel or any conducting means such as a tube or catheter, a needle or cannula or a needle-less system based on liquid jet or a particle gun with gas propellant. As known per se the outlet can be temporarily covered by a cap or, in connection with needles, a displaceable needle-guard. The container content material shall be deliverable by use of a delivery mechanism, also referred to herein as a pump, and any material fulfilling this requirement can be used. Normally the material is a fluid and preferably a liquid, including materials behaving as liquids such as emulsions or suspensions. These observations relates to the final-preparation whereas other components, notably solids, may be present before final preparation. The nature of container preparation content shall also be understood to include medical in broad terms and to embrace for example natural components and body fluids prefilled or drawn into the container although most commonly the medical is factory prepared. The device can be used in connection with medicals requiring a preparation step immediately prior to the infusion, typically a mixing of two or more components, which all may be fluid or may include a solid as when dissolving a lyophilized powder in a solvent, such as hormones or prostaglandins. The administration manner can also be varied within broad limits and may include entirely continuous infusion, continuous infusion with varying flow or intermittent infusions or injections with repeated either equal or varying doses. In portable devices the intermittent administration is common. Similarly, although injection devices may be contemplated also for a single dosing operation, generally they are designed for more than one or multiple individual doses for intermittent administration. In addition to the basic functions for delivery purposes the delivery system with preference may include other valuable features such as for initiating the container and its content and provide various checks and controls of both the container and the pump part electronics and mechanics. The mechanism for delivery of medical through the container opening should basically include at least one type of pump which may have to be selected for the special kind or container and medical used. The pump may include any kind of pressure source, such as mechanical or electrolytic pressure build-up, in the container and suitable valve means for control, which method can be used with virtually any kind of container and any kind of product, such as transdermal delivery of powder, similar delivery through liquid jets or regular tube infusion. The common syringe type container need a specialized pump system. Either the mechanism is adapted to act on complete syringes, having their own piston rods or the mechanism has a piston rod acting more or less directly on the piston of a cartridge type container, which can be made smaller and more adapted to portable devices. Also dual or multiple chamber cartridges can use similar devices for its various phases.

The system of the present invention comprises at least one injection device and a set of at least two elements, which elements are different in at least one respect or property. The property may be any of the above indicated shape, information or functional respects but can be any other property as well. Preferably the property is one that is significant for the user of the device and most preferably a property that is significant to the user as an individual. The existence of two, several or a plurality of different elements means that a choice can be made and that the device can be given different properties. This is not only an advantage for the user. It also represents an advantage to a manufacturer, supplier, vendor, wholesaler, retailer etc. since one and the same basic device can be modified into several varieties, which lowers costs, facilitates logistics etc. The minimum requirement on the system is that there shall be a possibility for such a modification. Devices may be delivered from the manufacturer with an attached selected element or a standard element for optional later replacement. Alternatively devices can be delivered naked for later selection and attachment, e.g. at a vendor or a physician. The attachment can be permanent, e.g. for security or safety reasons, by use of for example interlocking means. The attachment can be made releasable only by means of a tool, e.g. in the possession of a physician for replacement or administration instructions. The attachment can be arranged manually releasable, e.g. to allow element replacement to the taste or in the discretion of the user. It is clear that the three minimum components of the system need not be at the same physical location to satisfy the requirement for modification possibility although this is also a possibility, e.g. if a kit of one injector device with several alternative elements is delivered to the user. The system can also be actually assembled, e.g. in case the housing has at least two sites for the elements, occupied by different elements.

Housing and element are preferably mutually adapted for the purpose of creating at least one specific site for the elements in a set of such elements. When attached to the site the element should be localized to that site. If movable when attached to the site, the element shall have a range of movement limited to a fraction of the housing dimensions. For most purposes it is preferred that the element is immobile when attached to the site. To this end the housing and/or the element can have guiding structures. The housing may have a basic topology of irregular or double-curved areas forming natural guiding structures for correspondingly shaped elements. Special guiding structures may be added, such as a rim, recess or platform to form a specific structurally defined seat for the element. It is preferred that the site or seat parts of the housing are designed so as to allow handling of the injector also without an element attached and preferably also these parts are sealed with respect to the housing interior, by being covered or integral with the rest of the housing, in order to prevent access or entrance of contamination with or without an attached element. Similarly the elements may have guiding structures fitting to housing details. Both parts can have complementary structures keying into each other at attachment. Although it is possible that the element is fixed to the site by gluing, fusing or similar methods it is preferred that fixation takes place by mechanical means, which among others facilitates attachment, increases flexibility, allows replacement and avoids contamination. Any known principles for mechanical attachment can be used. Preferred are attachments based on shape and/or friction. The shapes of housing and element may be such that the element encircles the housing or a housing part to such an extent that locking and release prevention are created, e.g. that the element encircles a generally cylindrical or tube formed housing or housing part to more than a half circle in cross-section as for a rings, sleeves, clamps etc. Another shape-based attachment is use of special locking structures of known kind, e.g. interlocking structures, hooks and eyes, pins and grooves, protrusions and undercuts etc. Alternatively or in addition friction can be relied on, normally requiring a force as between interlocking structures or between housing and element, the latter preferably in combination with a design encircling the housing or housing part as described and preferably with a design of the element such that it has sufficient elasticity and prestress in its seated condition to generate a clamping force. Friction increasing structures, textures or material can be positioned on the housing site and/or preferably on the element inner surface. As indicated above the mechanical attachment can be designed for permanent fixation, tool releasable fixation or preferably manually releasable fixation.

An element can be said to have an "inner" surface adapted for attachment to the housing site and an "outer" surface exposed to the user. It is normally the inner surface that is provided with the attachment structures and features exemplified, although the whole element may contribute as in case of clamping. A "set" of elements shall be understood as a plurality of elements designed for attachment to the same type of site, i.e. having sufficiently similar inner surfaces or attachment characteristics to allow all of them be attached to the same site. Also fulfilling the requirements of a set are elements where a part can be exchanged, e.g. a translucent or transparent cover part for exchange of different sheets beneath although in most situations it is preferred that that the entire element is exchanged. It is possible that the housing has more than one site with the same kind of attachment characteristics, allowing attachment of the elements in a set to either or all such sites, e.g. two similar panels on each side of the housing or encircling element structures at different axial parts of the housing I is certainly also possible that the housing has a second or more types of sites for a second or more sets of elements having different attachment characteristics compared to the first set, e.g. a first site type and set for information and a second or more site types and sets for gripping or any other function. Different caps or needleguards may form one or two sets of element within the present meaning. When having more than one site type it is desirable the sets comprises elements that match between the sets in functional, ergonomic and/or aesthetical respects.

The attachment characteristics between housing and element can be designed so as to allow attachment in a movable manner, as indicated above, or at least to allow attachment of the element in more than one way, e.g. to relieve the user from considering what is left/right, front/rear etc. in case of symmetrically designed elements. In many instances it is preferred that the elements can be attached in only one fixed orientation, e.g. when dictated by function or asymmetry. The outer surface of the element may extend over substantially the same area as the inner surface or the housing site or seat but may also extend beyond such an area, e.g. for set of elements allowing variation of gripping areas, but the elements may also have the same overall shape, e.g. for other purposes. The nature of the outer surface is dependent on its function, and variations will be evident from the exemplification. The same applies for the overall shape of the element. A preferred class of shapes is "shell" formed elements, meaning that they substantially conforms to surface area of the housing and essentially forms a continuation of the housing exterior when attached although with slight deviations such as slightly recessed or elevated or with about the same elevation, e.g. when placed in a recess in the housing so as to make the element about flush with the surrounding housing exterior. To act as a shell in this meaning the element with preference is "thin" with respect to housing dimensions, e.g. less than 6 mm, preferably less than 4 and most preferably less than 2 mm. The shell can have varying cross-section thickness over its surface but preferably the shell has about constant cross-section thickness. The element or shell may cover the entire housing although modification advantages are reached it the element only occupies a part, e.g. less than 50% and preferably less than 30% of the housing total area, for example when applied only where functionally needed or sufficient for displaying information. It is preferred that the element only partly encircles the housing circumference. It is also preferred that the element only partly extends along the housing axis. To be further explained below, a shape found useful is a shell having substantially U-shaped cross-section and designed to clamp around slightly more than half a housing circumference and having an axial extension of less than housing length but more than the diameter of the U-shaped cross-section, preferably more than 2 and most preferably more than 3 timed the diameter.

BRIEF DESCRIPTION OF THE DRAWINGS

While the specification concludes of claims particularly pointing out and distinctly claiming the invention, it is believed the same will be better understood from the following description taken in conjunction with the accompanying drawings in which:

FIG. 5 is a cross section view of an element according to present invention;

FIGS. 6-14 are cross section views of alternative, contemplated embodiments of an element according to present invention, wherein FIG. 10 also is a cross section view along line A-A and FIG. 11 also is a cross section view along line B-B in FIG. 4;

FIG. 15 is an elevation view of the embodiment in FIG. 12; and

FIG. 16 is an exemplifying embodiment of an element according to present invention having a protruding fastening element for attaching a charm, a mascot or an anchoring chain to the injection apparatus of FIG. 1.

Figure 1:
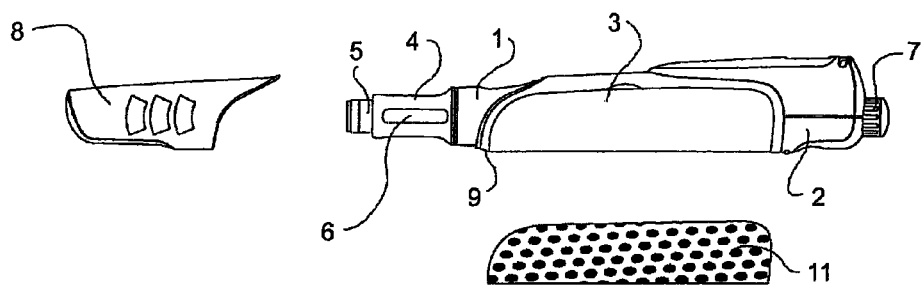
FIG. 1 in an exploded side view shows a pen-type injection device without the injection needle but exposing a needle mounting and its protecting cap, whereby two elements according to present invention are depicted below the handle section of the injection device.

The embodiments set forth in the drawings are illustrative in nature and not intended to be limiting of the invention defined by the claims. Moreover, individual features of the drawings and the invention will be more fully apparent and understood in view of the detailed description.

DETAILED DESCRIPTION OF THE INVENTION

Reference will now be made in detail to various embodiments of the invention, examples of which are illustrated in the accompanying drawings, wherein like numerals indicate similar elements throughout the views.

Referring first to FIG. 1 illustrating a portable multidose device in the form of a pen-type injector, said device generally comprises an injection moulded casing or housing consisting of a first end portion 1 and a second end portion 2. A handle section 3 or an area part of the housing serving as a handle is integrated in the second end portion between the ends of the casing. An injection outlet 4 is attached to the outermost end of the first end portion 1. In the illustrated embodiment the injection outlet is provided with a mounting (external threads) 5 for fastening of an injection needle (not shown) and has a cavity 6 adapted to receive an ampoule or container (not shown) holding a drug or a medical preparation to be self-injected by the owner of said injection apparatus. A mechanism for injecting a dose of a drug is housed inside said casing and FIG. 1 depicts a button 7 at the opposite end of the casing serving both as a dosing device and a trigger for the injection action. An optional protecting cap 8 is removably attached to said first end portion and protects the injection outlet when the injection device not is used.

The handle section 3 is encircled by an endless rib or ridge 9 defining a kind of seat and the ridge is integrated in the casing. However, said seat is not mandatory for present invention and in one presented embodiment of the invention (cf FIG. 6) it is preferable eliminated, ie the ridge 9 is missing.

Figure 2:
FIG. 2 illustrates the injection device of FIG. 1 in an assembled state and with a grip means according to present invention having a textured surface for gripping.
Figure 2:
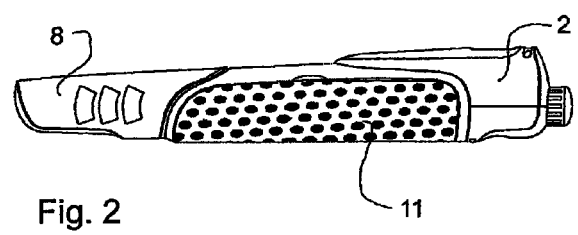

In order to customize the injection device to the user's or owner's personal requirements, needs and to provide vital information to medical personnel regarding the state of health or treatment of the user an element 11 has been invented, which is intended to be removable placed over the handle section 3 by the user of an ordinary portable injection device, eg the pen-type injector of FIG. 1. This personal element 11 is an essentially shell-formed element having a curved inner face 12 possessing a configuration substantially conforming to the shape of the handle section or said seat and has a length corresponding thereto. Thus, when mounted said element 11 preferably occupies the whole seat (if any) and works as a grip for the injection device. In cross section said element 11 is substantially U-shaped and is clamped over the handle section, cf FIGS. 2 and 5. As shown in FIG. 5 said cross section is more than semi circular and less than a full circle. This means that, when applying the element 11 on the handle section, the legs of the "U" is resiliently forced apart and then they will spring back and clamp fastened to the handle section 3. If the owner of the injection device wants to substitute the element 11 he just has to bend it lose, remove it and put another, preferred element in its place, cf the substitute element 11' depicted in FIG. 1, by pushing it sideways over the handle section 3. If, for any reason, the owner wants to keep the originally chosen element he may of course fasten it by means of an adhesive.

In above paragraph it is stated that the element 11 of present invention is U-shaped in cross section. However, said element may alternatively be of a substantially tubular design having an inner face 12 conforming to the shape of the handle section 3, schematically illustrated in FIG. 6. In this case the element 11 is positioned by sliding it lengthwise over the casing until it is in register with the handle section 3.

Referring now to FIG. 5 the element 11 preferably has a friction enhancing structure 13, eg grooves, small protrusions with sharp edges, particulate material integrated in the inner face 12 and so on, to eliminate the chance of the applied element sliding on the slippery surface of the handle section 3. Alternately or in addition to said structure the inner face 12 may be provided with a friction enhancing coating, e.g. a layer of rubber-based material.

An other way of fixing the element 11 on the handle section 3 is by a detent-recess lock. An example of said fixation is schematically illustrated in FIG. 7. A number of detents or small pins 14 protrude from the inner face 12 of the element 11 to be snapped into correspondingly shaped, interengaging recesses or holes 15 in the handle section.

Referring to FIGS. 8 and 9 the element 11 according to present invention alternately is composed of two or more materials permanently joined in the axial direction and/or the radial direction of said element. FIGS. 8 and 9 are cross section views showing two examples thereof. When the element has more than one layer the innermost layer 16 is of a more pliable material than that of the handle section 3 but less than that of a superimposed layer 17. As the innermost layer 16 works as an anchoring means it is made of resilient material and is rather thin. The superimposed layer 17 of elastic material is the actual grip portion and is softer and thicker than the layer 16 to give the user of the injection device a feeling of comfort and a steady holding of the injection device, when used. Preferably, the superimposed layer is a material possessing low thermal conductivity giving the user a pleasant feeling of warmth when handling the injection device. FIG. 9 illustrates that, according to one embodiment of the invention, a friction enhancing coating or layer 18 encloses the element 11. This layer 18 is thinner than layers 16 and 17 to be easily deformed and flexibly accompany any depression of the thicker layer 16 when the user squeezes the element 11. Alternately or in addition to said layer 18 the outer face of the element 11 possesses a friction enhancing structure similar to the one discussed above in conjunction with FIG. 5. Actually, all embodiments of the element of present invention preferably has an outer face made non-slippery, cf FIG. 2.

Figure 4:
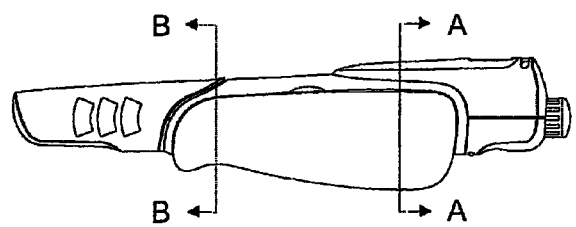
FIG. 4 schematically depicts the injection device of FIG. 2 and with a grip means according to present invention having a contour matching the palm and the fingers of the user of said device.

In order to better adapt the element 11 to the configuration of the hand of the user of the injection device or to his handling ability or wishes the soft grip layer 17 may be provided with portion(-s) 21 of a thickness larger than the general thickness of the element 11 and/or with portion(-s) 22 of a thickness smaller than the general thickness of the element, cf FIGS. 10 and 11, respectively. Preferably the element is given a contour matching the palm and fingers of the specific hand with which the user handles the injection device, cf FIG. 4. Said contour is preferably pre-made but could of course be configured afterwards.

Figure 3:
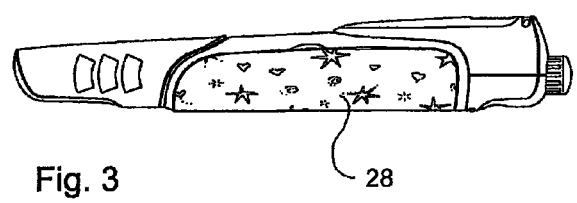
FIG. 3 illustrates the injection device of FIG. 2 but with an outer face provided with an elected pattern.

To make it possible to distinguish injection devices of the same brand from each other the elements according to present invention are envisaged to be available with an outer face 19 having a specific pattern 28 and/or colour(-s) chosen by the owner of the device, an example of which is presented in FIG. 3. When the owner wants to give the device a new and different appearance he has only to substitute said element.

Instead of or as a complement to the specific pattern 28 provided on the outer face 19 a sign, a bar-code, braille or characters are suitable incorporated in the surface. Hereby it is possible to display information regarding the owner of the injection device and/or dosing instructions to the user. Thus, a lost device is identified by the name and address printed on the outer face of the element. Of still more importance is the opportunity to provide the device with vital medical instructions such as kind of drug administrated by the injection device, dosing instructions, warning sign etc. This information would be very helpful for a medical attendant who is to treat an unconscious injection device user and could be a question of life and death.

An other way to give personal information about the owner and/or his medical needs is to produce the element 11 of a translucent or transparent material 17' and position a paper, sheeting film or the like 16', having said information and/or pattern, between the handle section 3 and the element 11, whereby the information is visible through the translucent layer 17' (cf FIG. 8).

The element 11 according to present invention even offers the opportunity to incorporate a chosen metering instrument in accordance with the owner's wishes or needs, such as a liquid crystal thermometer denoting the temperature of the drug ampoule, a blood sugar meter enabling the user to test himself and/or other beneficial meters. Some persons would like to have a digital watch or a magnetic tape with recorded information attached to the device. As an example of this FIGS. 12 and 15 show an element 11 according to present invention having a thermometer 23 integrated in said superimposed layer 17 and in level with said outer face 19.

It is also possible to give the injection device a specific (perfume) scent by enclosing micro-ampoules 24 containing an aromatic substance in the outer layer, eg said superimposed layer 17, as illustrated in FIG. 14.

Some persons appreciate a warm grip on an injection device and FIG. 13 depicts a heat reflective sheet 25 enclosed in the outer layer 17 adjacent to or at the outer face 19 of the element 11.

It is also popular among some groups of persons to have a personal item dangling from a belonging. This demand is fulfilled according to present invention by a ring-shaped mount, an eye, a protrusion with a through hole, a clamp or a similar device which is firmly attached to or integrated in said element for optional fastening of a string, a thread, a chain etc carrying a charm, a mascot or the like (not shown).

Thus, FIG. 16 shows a protrusion 26 with a through hole 27 arranged on the outer face 19 of the element 11. A similar attachment can alternatively be arranged on the housing itself, e.g. at the rear not to interfere with handling of the device.

Preferably said protecting cap 8 of the injection device has an outer face provided with a pattern, one or more colours, characters, a sign or the like matching that of the outer face of the element 11.

A variety of embodiments of present invention have been exemplified in the description and the drawings and the features presented therein may of course be optionally combined in the element of present invention according to the requirements of the user of the injection device.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What we claim is:

1. An injection device suitable for modification, the injection device comprising:
   a) a housing designed or suitable for manual gripping at a handle;
   b) a container for a preparation attachable to the housing;
   c) an outlet for the preparation exposed with respect to the housing;
   d) a mechanism arranged for moving the preparation from the container through the outlet; and
   e) at least one releasable, interchangeable element, wherein:
      each of the at least one element has an outer face possessing a structure, configuration and a function fulfilling personal requirements of the user;
      each of the at least one element being attachable to the housing via the seat of the housing;
      each of the at least one element being adapted to be brought into releasable clamping engagement with the handle in the seat;
      each of the at least one element is U-shaped in cross-section, having a curved inner face possessing a configuration substantially conforming to the shape of the handle, and having legs which are configured to resiliently force apart and spring back to allow the element to be brought into releasable clamping engagement with the handle, and wherein the legs curve in towards a center axis of the element; and
      each of the at least one element has a length essentially corresponding to the length of the handle and serving as a grip for the injection device;
      and wherein the handle comprises a ridge forming a site or seat to which is attachable at least one element.

2. The injection device according to claim 1, wherein the at least one element comprises a plurality of elements and where each of the plurality of elements is different in at least one respect or property.

3. The injection device according to claim 2, wherein the plurality comprises a first element and a second element, and where the first element is different from the second element in at least one respect or property selected from the group consisting of information carried, aesthetic properties, functional properties, size or shape or combinations thereof.

4. The injection device according to claim 3, further comprising a protecting cap with an outer face provided with a pattern, one or more colors, characters, a sign or the like matching that of the outer face of the element.

5. The injection device according to claim 3, wherein the inner face of the at least one element has a friction enhancing structure and/or a friction enhancing coating.

6. The injection device according to claim 3, wherein the at least one element has protrusions projecting inwardly from its inner face and arranged to fixingly engage with complementary shaped recesses in the handle of the injection device.

7. The injection device according to claim 3, wherein the at least one element comprises one or more materials more pliable than the material of the handle.

8. The injection device according to claim 7, wherein the one or more materials of the at least one element include an inner layer of a first resilient material and a superimposed layer of a second elastic material softer than the first material.

9. The injection device according to claim 8, wherein the one or more materials of the at least one element comprises an outer layer having an outer face possessing a friction enhancing structure and/or a friction enhancing coating.

10. The injection device according to claim 8, wherein at least two of the layers of the element are of mutually different thicknesses.

11. The injection device according to claim 3, wherein at least one element includes at least one portion having a thickness substantially larger than the general thickness of the element.

12. The injection device according to claim 11, wherein the at least one element has a contour matching the palm and the fingers of the user.

13. The injection device according to claim 3, wherein the at least one element includes at least one portion having a thickness substantially smaller than the general thickness of the element.

14. The injection device according to claim 13, wherein the at least one element has a contour matching the palm and the fingers of the user.

15. The injection device according to claim 3, wherein the outer face of the at least one element is provided with a pattern, one or more colors, characters, a sign, or any combination thereof.

16. The injection device according to claim 15, wherein the outer face of the at least one element is provided with the name of the user, dosing instructions, Braille, a bar code, or any combination thereof.

17. The injection device according to claim 15, wherein the outer face of the at least one element is painted with a fluorescent dye.

18. The injection device according to claim 3, wherein the at least one element is translucent, whereby a paper, sheeting, film or the like provided with a pattern, characters, a sign or information positioned between the handle section and the element is visible therethrough.

19. The injection device according to claim 3, further comprising a magnetic tape, a liquid crystal thermometer, a blood sugar meter and/or a digital watch integrated in the outer layer of the at least one element.

20. The injection device according to claim 3, further comprising one or more micro-ampules containing an aromatic substance arranged in the outer layer of at least one element.

21. The injection device according to claim 3, further comprising a heat reflective sheet enclosed in the outer layer of the at least one element.

22. The injection device according to claim 3, further comprising a ring-shaped mount, an eye, a protrusion with a through-hole, a clamp or a similar device firmly attached to or integrated in the at least one element for optional fastening of a string, a thread, a chain carrying a charm, a mascot, or any combination thereof.

* * * * *